(12) United States Patent
Corcoran et al.

(10) Patent No.: US 7,749,238 B2
(45) Date of Patent: *Jul. 6, 2010

(54) OCCLUSION DEVICE WITH FLEXIBLE POLYMERIC CONNECTOR

(75) Inventors: Michael P. Corcoran, Woodbury, MN (US); Joseph A. Marino, Apple Valley, MN (US)

(73) Assignee: Cardia, Inc., Eagan, MN (US)

( * ) Notice: Subject to any disclaimer, the term of this patent is extended or adjusted under 35 U.S.C. 154(b) by 1052 days.

This patent is subject to a terminal disclaimer.

(21) Appl. No.: 11/455,427

(22) Filed: Jun. 19, 2006

(65) Prior Publication Data

US 2007/0293891 A1 Dec. 20, 2007

(51) Int. Cl.
*A61B 17/08* (2006.01)
(52) U.S. Cl. .................. 606/151; 606/157; 606/158; 606/213
(58) Field of Classification Search .......... 606/151, 606/157, 158, 213
See application file for complete search history.

(56) References Cited

U.S. PATENT DOCUMENTS

| | | | |
|---|---|---|---|
| 3,874,388 A | 4/1975 | King et al. | |
| 4,007,743 A | 2/1977 | Blake | |
| 4,284,166 A | 8/1981 | Gale | |
| 4,917,089 A | 4/1990 | Sideris | |
| 5,019,057 A * | 5/1991 | Truckai | 604/527 |
| 5,092,424 A | 3/1992 | Schreiber et al. | |
| 5,108,420 A | 4/1992 | Marks | |
| 5,171,259 A | 12/1992 | Inoue | |
| 5,284,488 A * | 2/1994 | Sideris | 606/213 |
| 5,334,137 A | 8/1994 | Freeman | |
| 5,334,217 A | 8/1994 | Das | |
| 5,382,260 A | 1/1995 | Dormandy, Jr. et al. | |
| 5,397,331 A | 3/1995 | Himpens et al. | |
| 5,425,744 A | 6/1995 | Fagan et al. | |
| 5,433,727 A | 7/1995 | Sideris | |
| 5,451,235 A | 9/1995 | Lock et al. | |
| 5,634,936 A | 6/1997 | Linden et al. | |
| 5,702,421 A * | 12/1997 | Schneidt | 606/213 |
| 5,709,707 A | 1/1998 | Lock et al. | |
| 5,725,552 A | 3/1998 | Kotula et al. | |
| 5,741,297 A | 4/1998 | Simon | |
| 5,904,703 A | 5/1999 | Gilson | |
| 6,024,756 A | 2/2000 | Huebsch et al. | |
| 6,174,322 B1 | 1/2001 | Schneidt | |
| 6,206,907 B1 | 3/2001 | Marino et al. | |
| 6,389,146 B1 | 5/2002 | Croft, III | |
| 6,551,344 B2 | 4/2003 | Thill | |
| 6,634,455 B1 | 10/2003 | Yang | |
| 6,656,206 B2 | 12/2003 | Corcoran et al. | |
| 2005/0043711 A1 | 2/2005 | Corcoran et al. | |

(Continued)

FOREIGN PATENT DOCUMENTS

DE 42 22 291 C1 1/1994

(Continued)

*Primary Examiner*—Darwin P Erezo
*Assistant Examiner*—Melissa Ryckman
(74) *Attorney, Agent, or Firm*—Kinney & Lange, P.A.

(57) ABSTRACT

An occlusion device includes a center assembly having a flexible section formed by a polymeric connector. The flexible polymeric connector gives the center assembly improved torque and flexure characteristics, which allows the occlusion device to better conform to the contours of the heart.

18 Claims, 4 Drawing Sheets

U.S. PATENT DOCUMENTS

| | | |
|---|---|---|
| 2005/0228434 A1 | 10/2005 | Amplatz et al. |
| 2005/0273124 A1 | 12/2005 | Chanduszko |
| 2006/0025854 A1 | 2/2006 | Lashinski et al. |
| 2006/0122647 A1 | 6/2006 | Callaghan et al. |
| 2007/0293889 A1* | 12/2007 | Corcoran et al. ............ 606/213 |
| 2007/0293890 A1* | 12/2007 | Corcoran et al. ............ 606/213 |
| 2008/0065148 A1* | 3/2008 | Corcoran et al. ............ 606/213 |

FOREIGN PATENT DOCUMENTS

| | | |
|---|---|---|
| EP | 0 362 113 | 4/1993 |
| EP | 0 541 063 | 9/1998 |
| GB | 2 269 321 A | 9/1994 |

* cited by examiner

OCCLUSION DEVICE WITH FLEXIBLE POLYMERIC CONNECTOR

BACKGROUND OF THE INVENTION

This invention relates to an occlusion device for repairing cardiovascular defects. More specifically, this invention relates to an occlusion device which has a center assembly including a flexible connector, which comprises a tube formed of a polymeric material. The flexible polymeric connector provides improved torque and flexure characteristics and allows the device to better conform to the contours of the heart.

Normally, permanently repairing certain cardiac defects in adults and children requires open heart surgery, a risky, expensive, and painful procedure. To avoid the risks and discomfort associated with open heart surgery, occlusion devices have been developed that are small, implantable devices capable of being delivered to the heart through a catheter. Rather than surgery, a catheter inserted into a major blood vessel allows an occlusion device to be deployed by moving the device through the catheter. This procedure is performed in a cardiac cathlab and avoids the risks and pain associated with open heart surgery. These occlusion devices can repair a wide range of cardiac defects, including patent foramen ovale, patent ductus arteriosus, atrial septal defects, ventricular septal defects, and may occlude other cardiac and non-cardiac apertures. There are currently several types of occlusion devices capable of being inserted via a catheter. The occlusion devices must have sufficient flexibility to accomplish the sharp and numerous turns in the body's vasculature.

Another challenge in deploying an occlusion device in the heart is the variations of the contours of the aperture the occlusion device is meant to close. In particular, when occluding septal defects, the uneven topography in the vascular and septal walls of the human heart makes it difficult to design a device that can adapt to such variations. The challenge in designing an occluder which conforms to the uneven topography is compounded by the fact that the contours of each defect in each individual patient are unique. Poor conformation to the defect results in poor seating of the occlusion device across the aperture, which decreases the ability of the device to successfully occlude the aperture.

Lack of conformation to the walls of the heart can place significant amounts of stress on the occlusion device and decrease its fatigue life, resulting in the failure of the device. Once deployed, different parts of the occluder may experience more or less stress as a result of the uneven topography. At some point, stressed parts of the occluder may break. Broken parts increase the likelihood of damage to the surrounding tissue and lead to patient anxiety.

Another obstacle which may be encountered is the difficulty in readily distinguishing the individual occluder elements in order to determine their position in relation to each other and allow for repositioning, while still maintaining the flexibility needed for better conformation.

Thus, there is a need in the art for an occlusion device that will occlude cardiac defects and will match the contours of the heart thereby increasing the life of the device and its sealing ability while reducing damage to the surrounding tissue. There is also a need for an occlusion device that prevents rotation of the individual occluder elements around the center post, while still maintaining the needed flexibility to properly position the device and successfully match the contours of the heart.

BRIEF SUMMARY OF THE INVENTION

The present invention is an occlusion device having a center assembly that includes a flexible polymeric connector. The occlusion device has a first occluding body and a second occluding body connected by the center assembly. The center assembly comprises a proximal hub, which is attached to the first occluding body, a distal hub, which is attached to the second occluding body, and a flexible connector, which comprises a tube formed of a polymeric material, extending between the proximal hub and the distal hub. The flexible polymeric connector increases the ability of the occlusion device to more accurately conform to the defect, while still allowing the device to be moved, deployed and retrieved using a catheter.

DETAILED DESCRIPTION

Figure 1A:
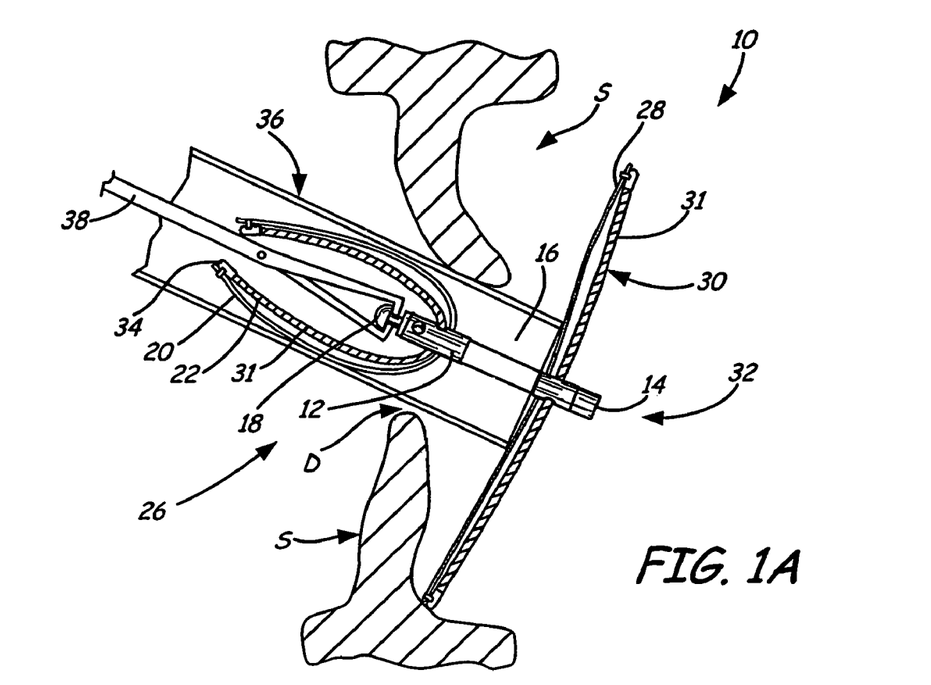
FIG. 1A-1B are diagrams of an occlusion device with a center assembly that includes a flexible polymeric connector being inserted into a defect.
Figure 1B:
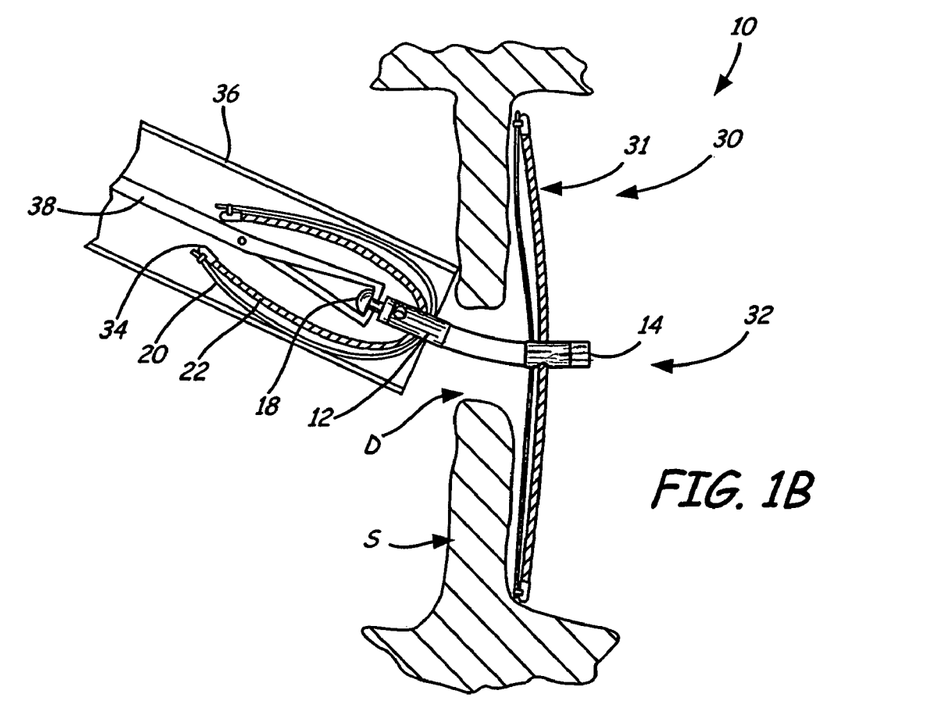

FIG. 1A-1B illustrate how occlusion device 10 having flexible polymeric connector 16 is deployed. Occlusion device 10 includes proximal hub 12, distal hub 14, flexible polymeric connector 16, knob 18, proximal support frame 20 and proximal sheet 22 (which form proximal occluding body 26), distal support frame 28 and distal sheet 30 (which form distal occluding body 32), and atraumatic tips 34. Also, shown are septal wall S, septal defect D, catheter 36, and delivery forceps 38.

Flexible polymeric connector 16 extends between proximal hub 12 and distal hub 14 to form a center assembly. (Methods of attaching flexible polymeric connector 16 to proximal and distal hubs 12, 14 will be discussed in detail with reference to FIG. 2.) Proximal and distal hubs 12, 14 may be comprised of any suitable material, including Nitinol (a nickel-titanium alloy), titanium or stainless steel. Flexible polymeric connector 16 is comprised of any suitable polymeric material, such as an elastomer. Flexible polymeric connector 16 is preferably formed to have a diameter of less than about 5 millimeters. In addition, the length of flexible polymeric connector 16 is preferably less than about 20 millimeters.

Proximal and distal support frames 20, 28 are attached to sheets 22, 30 in any suitable manner, such as with sutures or by molding sheets 22, 30 directly around proximal and distal support frames 20, 28 to form proximal occluding body 26 and distal occluding body 32. Proximal and distal support frames 20, 28 may be comprised of any number of arms (although only two arms of each of frames 20 and 28 can be seen in FIG. 1). One method of connecting the arms to proximal and distal hubs 12, 14 is to provide proximal and distal hubs 12, 14 with drill holes through which the arms extend. Atraumatic tips 34 are located at the distal end of each arm and serve to minimize damage to the surrounding tissue. Atraumatic tips 34 provide a place for sutures to attach sheets 22, 30 to proximal and distal support frames 20, 28. One method of suturing sheets 22, 30 to proximal and distal support frames 20, 28 is to provide atraumatic tips 34 with drill holes through which sutures pass. In this way, sheets 22, 30 are sewn to support frames 20, 28 at atraumatic tips 34. Proximal support frame 20 is connected to proximal hub 12. Distal support frame 28 is connected to distal hub 14.

More specifically, occlusion device 10 is constructed so that proximal and distal support frames 20, 28 are easily collapsible about proximal and distal hubs 12, 14. Due to this construction, occlusion device 10 can be folded so that proximal and distal support frames 20, 28 are folded in an axial direction. Proximal and distal sheets 22, 30, which are attached to proximal and distal support frames 20, 28, are flexible, and can likewise collapse as proximal and distal support frames 20, 28 are folded. In addition, proximal hub 12 further comprises knob 18, which allows for occlusion device 10 to be grasped by forceps 38 as it is inserted into the body through catheter 36.

Once occlusion device 10 is deployed, support frames 20, 28 must serve to hold proximal and distal sheets 22, 30 in place to seal defect D. To ensure there is sufficient tension to hold sheets 22, 30 in place, support frames 20, 28 are made of a suitable material (such as Nitinol) that is capable of shape memory. Nitinol is preferably used because it is commercially available, very elastic, non-corrosive, and has a fatigue life greater than that of stainless steel or titanium. To further ensure that support frames 20, 28 do not suffer from fatigue failures, support frames 20, 28 may be made of stranded wire or cables.

Sheets 22, 30 are comprised of a medical grade polymer in the form of film, foam, gel, or a combination thereof. Suitable materials may include DACRON® or polyurethane. Preferably, a high density polyvinyl alcohol (PVA) foam is used, such as that offered under the trademark IVALON®. To minimize the chance of occlusion device 10 causing a blood clot, foam sheets 22, 30 may be treated with a thrombosis inhibiting material, such as heparin.

The size of sheets 22, 30 may vary to accommodate various sizes of defects. When measured diagonally, the size of sheets 22, 30 may range from about 10 millimeters to about 45 millimeters. In some instances, it may be desirable to form sheets 22, 30 so that they are not both the same size. For instance, one sheet and its associated fixation device can be made smaller (25 millimeters) than the corresponding sheet and its associated fixation device (30 millimeters). This is particularly useful in situations where occlusion device 10 is to be placed at a location in the heart which is close to other nearby cardiac structures. Making sheets 22, 30 different sizes may assist in providing optimal occlusion of a defect, without affecting other structures of the heart which may be nearby.

FIG. 1A illustrates occlusion device 10 being inserted into septal defect D, which is one example of a cardiac defect that may be occluded using occlusion device 10. Occlusion device 10 is being inserted into septal defect D from catheter 36. Occlusion device 10 is held by delivery forceps 38. To insert occlusion device 10, catheter 36 is positioned proximate septal defect D. Next, delivery forceps 38 is used to push occlusion device 10 through catheter 36 so that distal occluding body 32 unfolds in the left atrium. Although distal occluding body 32 has been deployed, proximal occluding body 26 is still folded in catheter 36.

The placement of catheter 36, or other means that guides occlusion device 10 to septal defect D, determines the location of and angle at which occlusion device 10 is deployed. Once catheter 36 is properly positioned at septal defect D, delivery forceps 38 is used to push occlusion device 10 through septal defect D. Distal occluding body 32 of occlusion device 10 is then allowed to expand against septal wall S surrounding septal defect D.

Polymeric connector 16 is flexible but remains inside catheter 36 and is therefore immobilized. If polymeric connector 16 of occlusion device 10 is not flexible (or flexible but immobilized), the center assembly must enter septal defect D following the same angle of insertion as catheter 36 or other delivery device. As a result, the insertion angle is limited by the catheter's angle of insertion.

Often, due to limited space, catheter 36 enters the heart at an angle that is not perpendicular to septal wall S. In this situation, occlusion device 10 cannot enter septal defect D properly because the line of the center assembly must follow the same line as catheter 36. Occlusion device 10 must be forced into septal defect D at an angle, which may cause the tissue surrounding septal defect D to become distorted. If the surrounding cardiac tissue is distorted by catheter 36, it is difficult to determine whether occlusion device 10 will be properly seated once catheter 36 is removed and the tissue returns to its normal state. If occlusion device 10 is not seated properly, blood will continue to flow through septal defect 32 and occlusion device 10 may have to be retrieved and redeployed. Both doctors and patients prefer to avoid retrieval and re-deployment because it causes additional expense and longer procedure time.

FIG. 1B shows occlusion device 10 with flexible polymeric connector 16 being inserted into defect D. In FIG. 1B, occlusion device 10 has been further advanced through catheter 36 to expose flexible polymeric connector 16.

Because polymeric connector 16 is flexible, the insertion angle of occlusion device 10 is not restricted to that of catheter 36. Occlusion device 10 can be easily inserted, because once flexible polymeric connector 16 is outside catheter 36, the angle of insertion can be changed by allowing flexible polymeric connector 16 to move. This variable insertion angle allows occlusion device 10 to enter defect D at an optimum angle, minimizing distortion of surrounding cardiac tissue. If the tissue is not distorted when occlusion device 10 is deployed, the seating of occlusion device 10 should not change drastically once catheter 36 is removed. Because occlusion device 10 can be properly seated at the first insertion, the number of cases that require retrieval and redeployment should decrease.

Figure 1C:
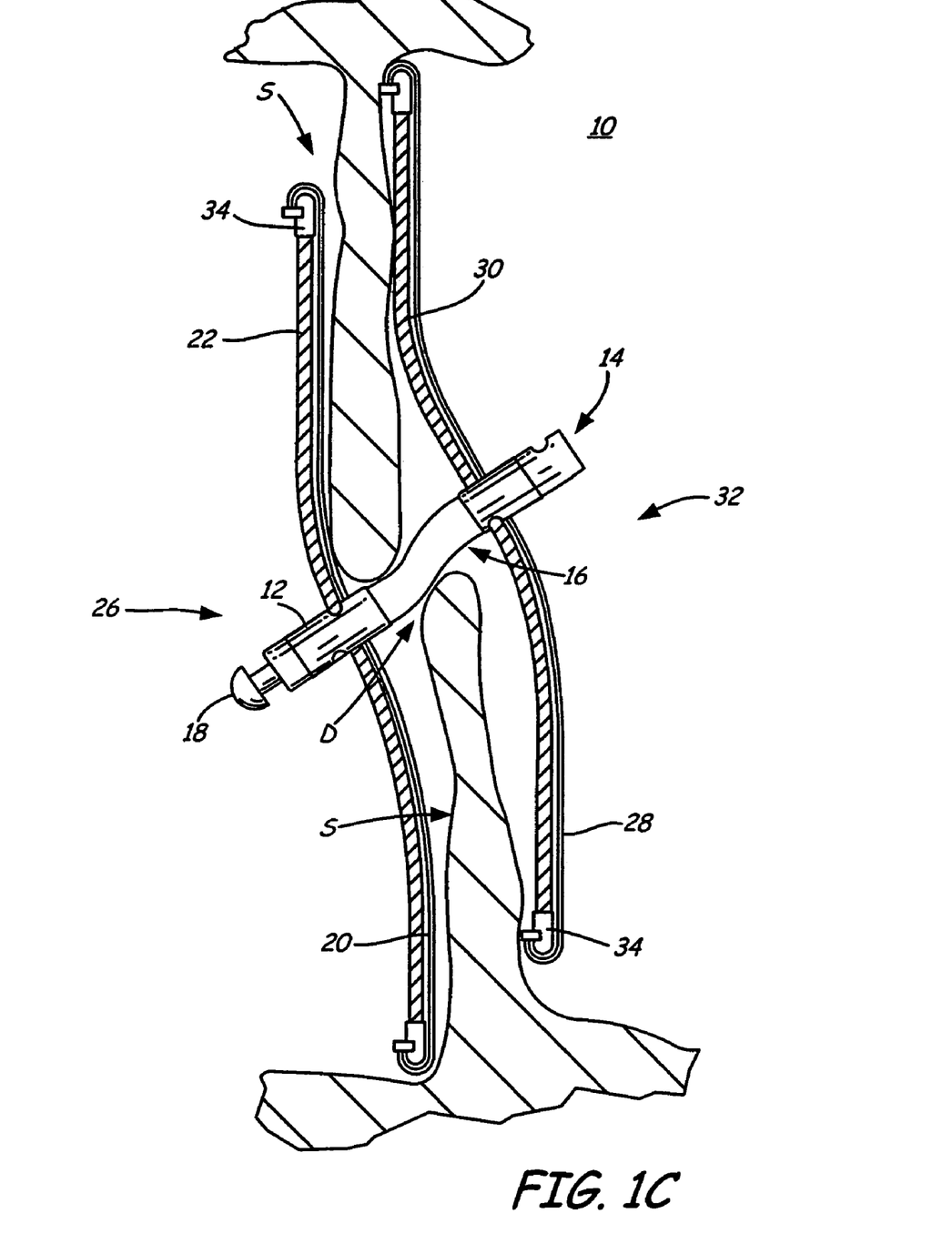
FIG. 1C is a diagram demonstrating the conformation capabilities of the occlusion device of FIGS. 1A-1B.

FIG. 1C shows occlusion device 10, which is fully deployed and is occluding defect D. Shown is occlusion device 10, which includes proximal hub 12, distal hub 14, flexible polymeric connector 16, knob 18, proximal support frame 20 and proximal sheet 22 (which form proximal occluding body 26), distal support frame 28 and distal sheet 30 (which form distal occluding body 32), and atraumatic tips 34. Also, shown are septal wall S, septal defect D, catheter 36, and delivery forceps 38.

By forming at least a portion of the center assembly to include flexible polymeric connector 16, the seating ability of occlusion device 10 is improved without the need for increased arm tension, which is necessary to occlude septal defect D or functionality (i.e. ability to move through a catheter, to twist or turn during deployment, to place against a septal wall) needed to properly deploy occlusion device 10.

Flexible polymeric connector 16 has no negative effect on the ability to move occlusion device 10 through catheter 36. This is because the length of flexible polymeric connector 16 is preferably less than about 20 millimeters. As such, flexible polymeric connector 16 is sufficiently rigid when necessary, such as when proximal and distal hubs 12, 14 are pushed toward one another when occlusion device 10 is moved through catheter 36.

At the same time, flexible polymeric connector 16 is capable of flexure. This flexibility of polymeric connector 16 allows for occlusion device 10 to be moved easily through sharp turns in a catheter, and allows for occlusion device 10 to be placed so that one side of occlusion device 10 is easily flexible relative to the other side.

Further, once deployed, flexible polymeric connector 16 is strong enough to hold proximal and distal occluding bodies 26, 32 of occlusion device 10 in place. Thus, flexible polymeric connector 16 provides the functionality required to deploy occlusion device 10, while offering the benefits of a fully flexible center connector.

In FIG. 1C, distal occluding body 32 has been properly positioned, proximal occluding body 26 has been deployed and occlusion device 10 has been released. FIG. 1C also demonstrates the ability of occlusion device 10 with flexible polymeric connector 16 to conform to an irregularly shaped septal defect D.

Another important advantage of the present invention is that flexible polymeric connector 16 allows distal and proximal occluding bodies 26, 32 to conform more readily to the contours of a heart after it is deployed, providing a custom fit to a variety of defects. Elastomeric material is capable of stretching and/or compressing to adapt to environmental changes and then return to its original shape when the deforming force is removed. Often, when implanted, occlusion device 10 is located in an irregularly shaped defect. Having flexible polymeric connector 16 allows occlusion device 10 to conform to a broader spectrum of defects because it is able to adjust and mold itself to the septal wall.

For instance, as viewed in FIG. 1C, septal wall S on the bottom of septal defect D may be only a few millimeters thick, but septal wall S on the top of septal defect D may be much thicker. In such cases, one side of occlusion device 10 may be bent open further than the other side. The side that is more distorted carries a high static load which increases pressure on the surrounding tissue and also increases the possibility of device fracture or septal tissue perforation. Because polymeric connector 16 is flexible, it can bend such that proximal and distal support frames 20, 28 need not be the only the only parts which adjust to fit septal defect D. The ability to conform to a variety of heart contours results in better seating, reduces arm tension (increasing fatigue life), and decreases the likelihood of damage to tissue resulting from device fracture.

Another feature of occlusion device 10 is that it is fully retrievable. To allow occlusion device 10 to be retrievable, as well as ensure that occlusion device 10 fits into a small diameter catheter, it is important to ensure that the arms of support frames 20, 28 are not of a length that results in atraumatic tips 34 clustering at the same location. If atraumatic tips 34 all cluster at the same location when occlusion device 10 is inside catheter 36, occlusion device 10 will become too bulky to allow it to be easily moved through catheter 36.

Figure 2:
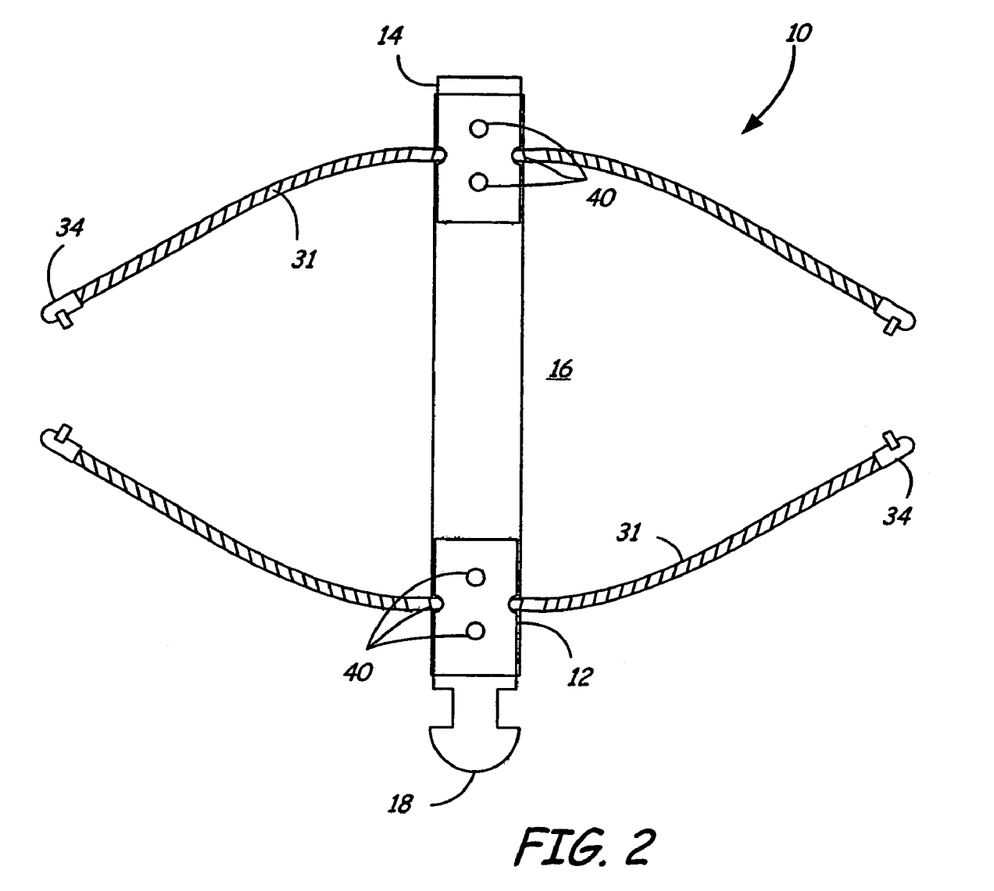
FIG. 2 a partial cross sectional view of the occlusion device of FIGS. 1A-1C.

FIG. 2 is a partial cross sectional view of occlusion device 10 which is shown in FIGS. 1A-1C. Occlusion device 10 includes proximal hub 12, distal hub 14 and flexible polymeric connector 16. Also shown is grasping knob 18, arms 31, atraumatic tips 34 and holes 40, which provide a location for attaching the occluding bodies, such as the wire support frames (shown in FIG. 1) to proximal and distal hubs 12, 14.

Flexible polymeric connector 16 extends between proximal hub 12 and distal hub 14. Proximal and distal hubs 12, 14 may be comprised of any suitable material, including Nitinol, titanium or stainless steel. Flexible polymeric connector 16 may be comprised of any suitable biocompatible, polymeric material, such as silicone. In the embodiment shown in FIG. 2, flexible polymeric connector 16 is comprised of an elastomer tube.

One method of attaching flexible polymeric connector 16 to proximal and distal hubs 12, 14 is to insert proximal and distal hubs 12, 14, which are sized to correspond to an overall diameter of flexible polymeric connector 16, into the proximal and distal ends of flexible polymeric connector 16. Flexible polymeric connector 16 is provided with drill holes, which correspond to holes 40 of proximal and distal hubs 12, 14. As shown in FIG. 2, arms 31 are inserted through flexible polymeric connector into holes 40 to secure flexible polymeric connector 16 in place. Other assembly methods include using a collar or pin to secure flexible polymeric connector 16 to proximal hub 12 and distal hub 14.

Flexible polymeric connector 16 is preferably formed to have an outer diameter of less than about 5 millimeters. In addition, the length of flexible polymeric connector 16 is preferably less than about 20 millimeters. Resulting flexible polymeric connector 16 is extremely flexible and also has an improved resistance to fatigue.

Given the nature of polymeric connector 16 and the manner in which it is attached to proximal and distal hubs 12, 14, polymeric connector 16 is extremely flexible, while retaining the ability to transmit rotational (i.e. torque) and axial (i.e. push and pull) forces. In addition to being capable of articulation, since flexible polymeric connector 16 is also capable of transmitting torque, it is possible to rotate occlusion device 10 during deployment. This allows better positioning and seating of occlusion device 10.

While it may be necessary to rotate occlusion device 10 during deployment, it is often not desirable for occluding bodies to be rotatable relative to flexible polymeric connector 16 or to one another. When the occluding bodies are attached to proximal and distal hubs 12, 14 (as described with respect to FIGS. 1A-1B), the occluding bodies will be prevented from rotating with respect to each other and to polymeric connector 16.

There are several disadvantages to allowing occluder elements to rotate around a connector. First, it is possible that the support arms of one support frame will line up with the arms of the other support frame, making it difficult to distinguish one set from the other set when the occlusion device is viewed on a fluoroscope. As a result, it is more of a challenge to determine the exact position of either support frame because when aligned, the two become indistinguishable.

Second, preventing rotation of the occluder elements may improve the overall positioning of the device. For example, when inserting a device that allows freedom of rotation, if upon the insertion of the device, the arms of a support frame are laying in an undesirable position, such as resting against the aorta, simply manipulating the device to reposition the arms may not be possible because the center assembly will spin relative to the occluder element, leaving the arms in the original position.

Third, the preliminary loading of the device may be hindered if rotation of the support frames is not prevented. When the individual occluder elements spin and twirl, loading the occlusion device into a delivery device or catheter may be more difficult and time-consuming.

Figure 3:
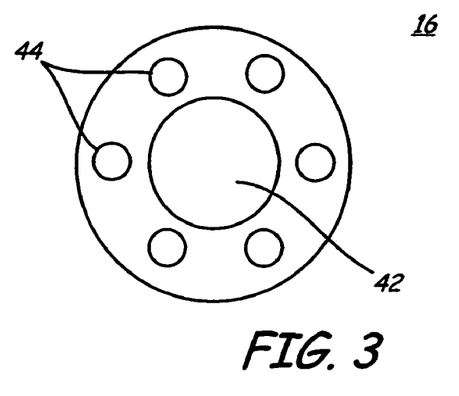
FIG. 3 is cross sectional view of a flexible polymeric connector.

FIG. 3 is cross sectional view of flexible polymeric connector 16. Shown is central lumen 42 and peripheral lumens 44. Flexible polymeric connector 16 is an elastomer tube having central lumen 42. Flexible polymeric connector 16 also includes peripheral lumens 44, which encircle central lumen 42. In FIG. 3, flexible polymeric connector is shown with six peripheral lumens 44. However, the present invention is not so limited and may include any number of peripheral lumens 44.

Figure 4:
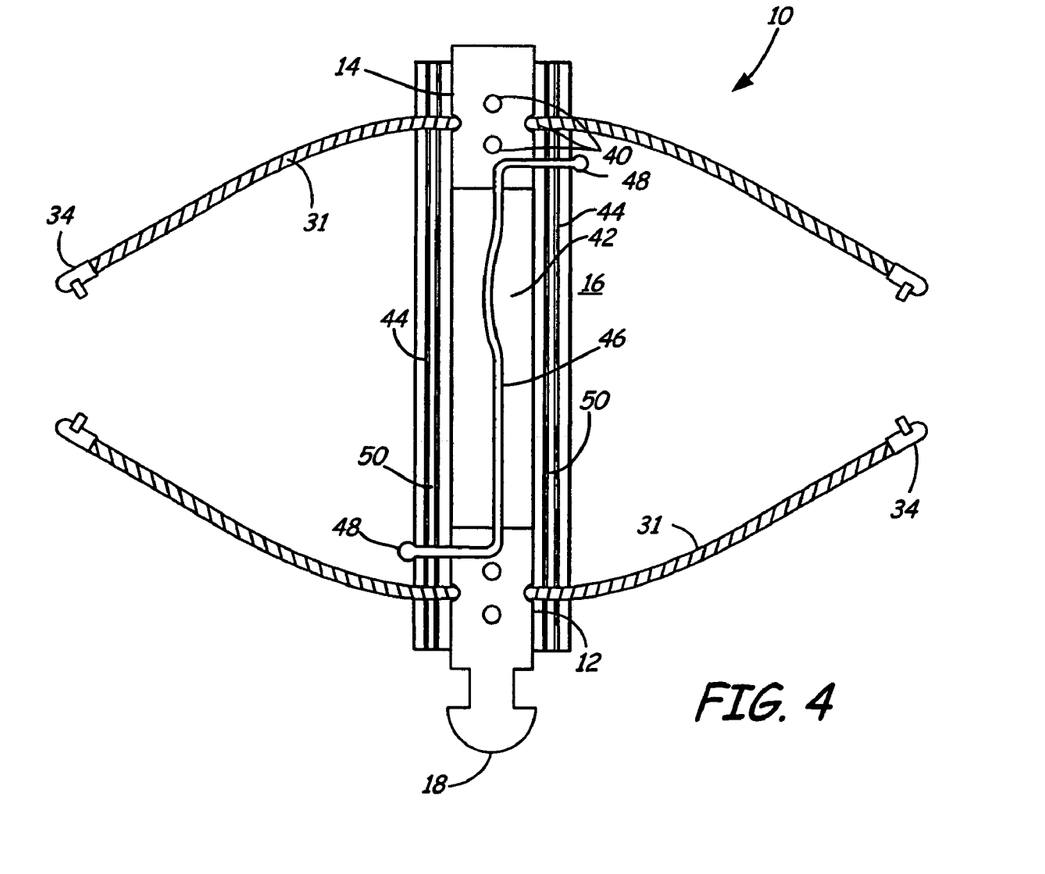
FIG. 4 is a partial cross sectional view of occlusion device having a flexible polymeric connector which includes a safety tether and support wires.

FIG. 4 is a partial cross sectional view of occlusion device 10, which includes proximal hub 12, distal hub 14 and flexible polymeric connector 16. Also shown is grasping knob 18, arms 31, atraumatic tips 34, holes 40, which provide a location for attaching the occluding bodies, such as the wire support frames (shown in FIG. 1) to proximal and distal hubs 12, 14, central lumen 42, peripheral lumens 44, safety tether 46, knots 48, and support wires 50.

As shown in FIG. 4, occlusion device includes safety tether 46, which serves to further ensure the structural integrity of occlusion device 10. Safety tether 46 connects proximal hub 12 to distal hub 14 and extends through central lumen 42 of flexible polymeric connector 16. Flexible polymeric connector 16 changes its shape in response to an external force. When the force is removed, flexible polymeric connector 16 returns to its original shape. Safety tether 46 serves to limit the extension of flexible spring connector 46 by becoming taut when too much pull force is applied. Safety tether 46 also ensures that proximal hub 12, flexible polymeric connector 16, and distal hub 14 remains fully connected while navigating the vasculature and during deployment in a heart. Safety tether 46 also aids in retrieval of occlusion device 10 because for retrieval to occur, occlusion device 10 must be pulled back through a catheter.

Safety tether 46 may be formed of any suitable material, including Nitinol, titanium, stainless steel or polymeric material. In addition, safety tether 46 may be comprised of a single wire or thread, or may be comprised of a multi-wire strand or cable or a multi-thread fabric braid.

As shown in FIG. 4, safety tether 46 is attached to proximal and distal hubs 12, 14 by threading it though a cavity in proximal and distal hubs 12, 14 and securing safety tether 46 to an outside surface of proximal and distal hubs 12, 14 with knots 48. However, safety tether 46 may be attached to proximal and distal hubs 12, 14 with any suitable method. For instance, a crimp ring could also be used to attach safety tether 46 to proximal and distal hubs 12, 14

Also shown in FIG. 4 are support wires 50, which serve to decrease the flexibility of flexible polymeric connector 16. Support wires 50 may be comprised of any suitable material, including Nitinol (a nickel-titanium alloy), titanium or stainless steel and may be single wires or multiple stranded wires. Support wires 50 are inserted into peripheral lumens 44 of flexibility of polymeric connector 16. More or less support wires 50 may be utilized, depending on the amount of flexibility needed.

Although the present invention has been described with reference to preferred embodiments, workers skilled in the art will recognize that changes may be made in form and detail without departing from the spirit and scope of the invention.

The invention claimed is:

1. An occlusion device comprising:
   a first occluding body;
   a second occluding body; and
   a center assembly comprising a flexible polymeric tube having a sidewall and a central lumen extending from a proximal end to a distal end of the tube, a proximal hub inserted into the central lumen at the proximal end of the tube, and a distal hub inserted into the central lumen at the distal end of the tube, wherein the first occluding body includes a plurality of arms that extend through the sidewall at the proximal end of the tube and through the proximal hub to attach the first occluding body to the proximal hub, and wherein the second occluding body includes a plurality of arms that extend through the sidewall at the distal end of the tube and through the distal hub to attach the second occluding body to the distal hub.

2. The occlusion device of claim 1 wherein an overall diameter of the flexible tube is less than about 5 millimeters.

3. The occlusion device of claim 1 wherein the center assembly further comprises a safety tether located within the flexible tube and extending between the proximal hub and the distal hub.

4. The occlusion device of claim 3 wherein the safety tether comprises a wire.

5. The occlusion device of claim 3 wherein the safety tether comprises a braided fabric.

6. The occlusion device of claim 1 wherein the flexible tube further comprises a plurality of peripheral lumens extending from the proximal end to the distal end.

7. The occlusion device of claim 6 wherein the flexible tube further comprises a plurality of wires extending through the plurality of peripheral lumens.

8. An occlusion device comprising:
   a flexible polymeric tube having a sidewall and a central lumen extending from a proximal end to a distal end of the tube;
   a proximal hub inserted into the central lumen at the proximal end of the tube;
   a distal hub inserted into the central lumen at the distal end of the tube;
   a first collapsible support frame having a plurality of arms that extend through the sidewall at the proximal end of the tube and through the proximal hub to attach the first collapsible support frame to the proximal hub;
   a second collapsible support frame having a plurality of arms that extend through the sidewall at the distal end of the tube and through the distal hub to attach the second collapsible support frame to the distal hub;
   a tether providing a safety connection between the tube, the proximal hub and the distal hub;
   a first sheet attached to the first collapsible support frame; and
   a second sheet attached to the second collapsible support frame.

9. The occlusion device of claim 8 wherein the first collapsible support frame is oriented relative to the second collapsible support frame to offset the arms of the first collapsible support frame from the arms of the second collapsible support frame.

10. The occlusion device of claim 8 wherein an outer diameter of the polymeric tube is less than about 5 millimeters.

11. The occlusion device of claim 8 wherein the polymeric tube is formed of elastomer.

12. The occlusion device of claim 11 wherein the polymeric tube further comprises a plurality of peripheral lumens extending from the proximal end to the distal end.

13. The occlusion device of claim 12 wherein the polymeric tube further comprises a plurality of wires extending through the plurality of peripheral lumens.

14. The occlusion device of claim 8 wherein the tether comprises a wire.

15. The occlusion device of claim 8 wherein the tether comprises a braided fabric.

16. An occlusion device comprising:
a first occluding body;
a second occluding body; and
a center assembly comprising a flexible polymeric tube having a sidewall and a central lumen extending from a proximal end to a distal end of the tube, a proximal hub inserted into the central lumen at the proximal end of the tube, and a distal hub inserted into the central lumen at the distal end of the tube, wherein the first occluding body includes a plurality of arms that extend through the sidewall at the proximal end of the tube and through the proximal hub to attach the first occluding body to the proximal hub, and wherein the second occluding body includes a plurality of arms that extend through the sidewall at the distal end of the tube and through the distal hub to attach the second occluding body to the distal hub.

17. The occlusion device of claim 16 wherein the center assembly further comprises a safety tether extending between the proximal hub and the distal hub.

18. The occlusion device of claim 17 wherein the safety tether extends through both the proximal end and the distal end of the tube.

* * * * *